United States Patent [19]

Ducheyne et al.

[11] Patent Number: 4,923,513
[45] Date of Patent: May 8, 1990

[54] TITANIUM ALLOY TREATMENT PROCESS AND RESULTING ARTICLE

[75] Inventors: Paul Ducheyne, Bryn Mawr; David H. Kohn, Philadelphia, both of Pa.

[73] Assignee: Boehringer Mannheim Corporation, Indianapolis, Ind.

[21] Appl. No.: 341,775

[22] Filed: Apr. 21, 1989

[51] Int. Cl.$^5$ .............................................. C22C 1/04
[52] U.S. Cl. .......................................... 75/245; 419/2; 419/23; 419/25; 419/29; 419/36; 419/53; 419/54; 419/55; 420/420; 148/126.1; 148/421
[58] Field of Search .................... 419/29, 2, 23, 25, 36, 419/53, 54, 55; 75/245; 420/420; 148/126.1, 421

[56] References Cited

U.S. PATENT DOCUMENTS

| | | | |
|---|---|---|---|
| 2,431,690 | 12/1947 | Hall et al. | 75/245 |
| 2,892,742 | 6/1959 | Zwicker et al. | 148/20.3 |
| 2,899,299 | 8/1959 | Lynch | 419/54 |
| 3,084,042 | 4/1963 | Wartel et al. | 419/54 |
| 4,012,230 | 3/1977 | Dickinson et al. | 419/25 |
| 4,219,357 | 8/1980 | Yolton et al. | 419/48 |
| 4,331,477 | 5/1982 | Kubo et al. | 75/228 |
| 4,505,764 | 3/1985 | Smickley et al. | 148/133 |
| 4,601,874 | 6/1986 | Marty et al. | 419/23 |
| 4,604,260 | 8/1986 | Shimizu et al. | 419/2 |
| 4,612,066 | 9/1986 | Levin et al. | 148/20.3 |
| 4,614,638 | 9/1986 | Kuroishi et al. | 419/39 |
| 4,655,855 | 4/1987 | Levin et al. | 148/20.3 |
| 4,680,063 | 7/1987 | Vogt et al. | 148/11.5 F |
| 4,689,077 | 8/1987 | Chevigne et al. | 75/233 |
| 4,714,587 | 12/1987 | Eylon et al. | 419/29 |
| 4,719,077 | 1/1988 | Suzuki et al. | 419/23 |
| 4,828,793 | 5/1989 | Froes et al. | 419/6 |

OTHER PUBLICATIONS

W. H. Kao et al, "Effect of Temporary Alloying by Hydrogen (Hydrovac) on the Vacuum Hot Pressing and Microstructure of Titanium Alloy Powder Compacts", *Progress in Powder Metallurgy*, vol. 37 (1981), pp. 289-301.
R. G. Vogt et al, "Thermo-Chemical Treatment (TCT) of Titanium Alloy Net Shapes", *Titanium Net Shape Technologies*, Edited by F. H. Froes et al (1984), pp. 145-153.
S. M. Soltesz et al, "Nontraditional Thermal Processing of HIP'ed Investment Cast Ti-6Al-4V Alloy", pp. 187-194 (date-unknown).
L. Levin et al, "Fatigue Resistance Improvement of Ti-6Al-4V by Thermochemical Treatment", in *Titanium, Science and Technology*, vol. 4, Edited by G. Lutjering et al, DGM, Oberursel, pp. 2107-2114 (1985).
Froes, F. H., and Fickens, J. R., "Powder Metallurgy of Light Metal Alloys for Demanding Applications", *Journal of Metals*, vol. 36, No. 1, Jan. 84, pp. 14-28.
Y. Mahajan et al, "Studies of Hydrogenation in Ti-6Al-4V Alloy", *Scripta Metallurgica*, vol. 13 (1979), pp. 695-699.
C. A. Kelto et al, "Titanium Powder Metallurgy-A Perspective", *Journal of Metals*, vol. 32, No. 8, Aug. 1980, pp. 17, 24, 25.
W. R. Kerr et al, "Hydrogen as an Alloying Element in Titanium (Hydrovac)", *Titanium '80 Science and Technology* (1980), pp. 2477-2486.
D. Eylon et al, "Property Enhancement of Titanium Alloys by Microstructure Modification", Paper No. 197 (1988), 7 pages.
C. F. Yolton et al, "Microstructure Modification of Titanium Alloy Products by Temporary Alloying with Hydrogen", Paper No. 21 (1988), 7 pages.

*Primary Examiner*—Stephen J. Lechert, Jr.
*Assistant Examiner*—Nina Bhat
*Attorney, Agent, or Firm*—Perman & Green

[57] ABSTRACT

A carefully controlled amount of hydrogen is diffused into titanium or its alloys at an elevated temperature above the transformation temperature. After the elevated temperature is maintained for an approprate duration of time, eutectoid transformation is performed in an inert atmosphere, again for an appropriate period of time, during which or alternatively after which the hydrogen is removed and the metal cooled to room temperature. A sintered titanium alloy component of the type intended for use as a joint replacement subjected to such a treatment displays a fatigue strength which is noticeably improved over a similar article with an equiaxed or lamellar microstructure.

41 Claims, 6 Drawing Sheets

400x

TITANIUM ALLOY TREATMENT PROCESS AND RESULTING ARTICLE

BACKGROUND OF THE INVENTION

1. Field of the Invention

The present invention relates to a heat treatment process for a titanium alloy which results in an end product having significantly improved fatigue qualities. The method is of particular benefit to medical prostheses, for example, joint replacement components, but may be of benefit in any environment requiring high strength, light weight components subjected to elevated, intermittent stresses.

The process calls for temporary diffusion into the metal alloy of a fugitive alloying element to promote a phase transformation in the metal. Hydrogen is of particular interest because it has significant effects on titanium alloys and can be readily removed from the metal after treatment. The alloy is then subjected to a controlled eutectoid transformation after which the fugitive alloying element is removed from the metal.

2. Description of the Prior Art

Hydrogen has previously been used to facilitate the workability of titanium and its alloys. It has been used to embrittle titanium to facilitate its comminution by mechanical means to form titanium metal powders. In such techniques hydrogen is diffused into the titanium at elevated temperatures, the metal is cooled and brittle titanium hydride formed. The brittle material is then fractured to form a powder. The powder may then have the hydrogen removed or a compact may be formed of the hydrided material which is then dehydrided. This process has been described in U.S. Pat. No. 4,219,357 to Yolton et al.

Hydrogen also has the effect of increasing the high temperature ductility of titanium alloys. This characteristic has been used to facilitate the hot working of titanium alloys. Hydrogen is introduced to the alloy which is then subjected to high temperature forming techniques such as forging. The presence of hydrogen allows significantly more deformation of the metal without cracking or other detrimental effects, as related in U.S. Pat. No. 2,892,742 to Zwicker et al.

Clearly our invention does not deal with enhancing the workability of titanium or its alloys, as in the above example. We focus on creating a microstructure with optimum resulting mechanical properties. Such approaches have been followed by others before us: hydrogen has also been used as a temporary alloying element in attempts to alter the microstructure and mechanical properties of titanium alloys. In such applications, hydrogen is diffused into the titanium alloys, the alloys cooled to room temperature and then heated to remove the hydrogen. The effect of the temperature of introducing and removing the hydrogen on the structure and properties of titanium alloys was investigated by W. R. Kerr et al, as part of a larger study, and their findings published in an article entitled: "Hydrogen as an Alloying Element in Titanium (Hydrovac),'- 'Titanium '80 Science and Technology (1980), pp. 2477–2486. In this study, some fundamentals of the so called temporary hydrogen alloying technique were analyzed. The study did not result in an optimum process. A first attempt thereto resulted in the disclosure of Smickley et al in U.S. Pat. No. 4,505,764. They disclose a process of treating a cast titanium alloy (e.g. Ti-6Al-4V) for the purpose of refining its microstructure. The casting is heated to a treatment temperature near, but below, the beta transformation temperature. A solute material, such as hydrogen, in the range of 0.2% to 5% by weight is diffused into the casting at the aforesaid treatment temperature below the beta transformation temperature. A refined structure is created next largely as the result of the reverse transformation and not necessarily as a result of a eutectoid transformation. Subsequently, the metal is allowed to cool to room temperature.

This process is inflexible in that the article must be maintained at high temperature until the last step is performed, i.e. the hydrogen removed. Our invention, in contrast, teaches now to process the article without having to be concerned about thermal cracking resulting from low temperatures during or between any of the steps of the process. Furthermore, the Smickley process can be highly inefficient in view of the very long transformation times needed with the amount of hydrogen that is indiffused uncontrollably during their process. Again, we have solved this drawback by inventing processing conditions yielding optimized hydrogen concentrations.

Levin et al, in U.S. Pat. No. 4,612,066, disclose a process for fabricating titanium alloy components which subsequent to being cast are first transformed to a martensitic structure. Similar processes have been disclosed by Levin et al in U.S. Pat. No. 4,655,855 for refining the microstructure of titanium alloy powder compacts and by Vogt et al in U.S. Pat. No. 4,680,063 for fabricating forged titanium alloy components.

Such a martensitic structure is obtained by rapidly cooling the article. Having the martensitic structure is essential to their invention, since the subsequent steps rely upon the presence of this structure to produce a microstructural refinement. In our invention we exclude the possibility of any martensite. Since phase transformation from a starting martensitic structure, as in Levin et al, or from a starting beta structure, as in our invention, are fundamentally different, Levin's disclosures are materially unimportant with respect to our invention.

SUMMARY OF THE INVENTION

In the instance of medical prostheses and, particularly, joint replacement components fabricated from titanium alloy, a preferred technique is to achieve cementless fixation by use of porous metal coatings which enable and attract bone ingrowth. However, typically, the process for achieving such a porous coating as, for example, the proprietary coating of DePuy Division of Boehringer Mannheim Corporation provided under the trademark "POROCOAT" calls for the item to be sintered. Sintering, by definition, requires that the item be heated to an elevated temperature at which the item maintains its solid state, but which, upon cooling, undergoes the beta to alpha plus beta transformation. This results in a microstructure which is coarser and with a different alpha/beta morphology than that achieved with deformation processing operations such as forging. These microstructures are usually associated with reduced dynamic low temperature properties such as fatigue strength. Unfortunately, forging can no longer be applied once the porous coating has been deposited since it would eliminate the beneficial pore structure of the coating.

Microstructural coarsening in a titanium alloy such as Ti-6Al-4V arises in the following manner. At the sintering temperature (upwards of 1000° C.), the material is a solid of the high temperature body center cubic (BCC) allotrope, which is referred to herein as beta. On cooling, the material reaches the beta transformation (beta transus) temperature where part of the beta transforms to the low temperature, hexagonal close packed (HCP) allotrope, which is referred to herein as alpha. In the case of the pure metal at room temperature, the microstructure consists entirely of alpha ("transformed beta") grains, the orientation of which relate to certain crystallographic planes of the prior beta phase, and the size of which relates to both the cooling time through the transformation temperature and the subsequent cooling rate. In the case of an alloy such as Ti-6Al-4V which is cooled at a slow or moderate rate, the material at room temperature exhibits a coarse two phase microstructure of alpha ("transformed beta") plus beta, because the example alloy contains sufficient alloying element content to stabilize some fraction of the beta to room temperature. The alpha plus beta transformation product of the high temperature beta phase (hereafter "transformed beta") has generally limited mechanical properties, particularly low temperature dynamic properties such as fatigue strength.

The present invention relates, in part, to the use of a "fugitive" solute to induce a phase transformation in a metal and in that manner refine the microstructure without the complications of forging or the limitations of conventional heat treatments. As will be set out in greater detail in following portions of the present disclosure, the solute has the effect of creating a phase transformation in ways neither possible nor obvious before and it results in mechanical properties at least as good as previously achieved. The solute is diffused into the metal as the metal is being heated to a temperature substantially above the transformation temperature or while the temperature of the metal is already substantially above the transformation temperature.

In our invention, the amount of hydrogen diffused into the metal is controlled to an optimum level, after which the metal is cooled and maintained at a temperature below the beta transus for a duration adequate to achieve a eutectoid transformation so as to produce a fine and uniform (alpha plus beta) or (alpha plus beta plus gamma) microstructure with a distinctly non-lamellar morphology. Thereafter, the hydrogen is diffused out of the metal and the metal cooled to room temperature.

The removable solute is used as a temporary alloying element in titanium metals and its alloys as a means to promote the alpha to beta or the (alpha plus beta) to beta phase transformation, under controlled conditions. In principle, a variety of low atomic number (e.g. less than about 16), and thus relatively mobile species might be used as a temporary solute. Based on the considerations given above, however, hydrogen appears to be a particularly desirable temporary solute especially for use with titanium and its alloys. Hydrogen increases the stability of the BCC phase relative to low temperature HCP phase since it is more soluble in the "relatively open" BCC structure. In addition, it is readily available; it is a gas which can be easily handled using more or less conventional pumping systems; it exhibits a very high mobility or diffusion rate in titanium alloys; and the compounds it forms with titanium are relatively unstable.

The amount of hydrogen controlled by our invention in the range of 0.70% to 0.90% by weight is diffused into the metal, a most likely candidate of which is Ti-6Al-4V, preferably at a temperature of approximately 850° C. for a duration of approximately one-half hour. Thereafter, eutectoid transformation is performed in an inert atmosphere, preferably in an atmosphere of argon gas, at a temperature of approximately 590° C. for a duration of approximately four hours. Then, dehydrogenation is preferably performed in a vacuum at a temperature of approximately 775° C. for approximately four hours, after which the metal is cooled to room temperature. An alternative preferred procedure is to combine the eutectoid transformation and dehydrogenation into one step by maintaining the article in an inert atmosphere at 650° C. for a duration of at least 8 hours.

A titanium alloy component subjected to the foregoing treatment is found to exhibit a reasonably fine microstructure. The resulting nominal alpha grain size is one micron or less. Furthermore, a sintered component which is similarly treated is found to have a yield strength and an ultimate tensile strength exceeding that of a similar non-sintered titanium alloy article having an equiaxed microstructure. Also, fatigue strength of such a sintered component is noticeably improved over the equiaxed microstructure article.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and, together with the description, serve to explain the principles of the invention in general terms.

DETAILED DESCRIPTION OF THE PREFERRED EMBODIMENTS

Figure 1:
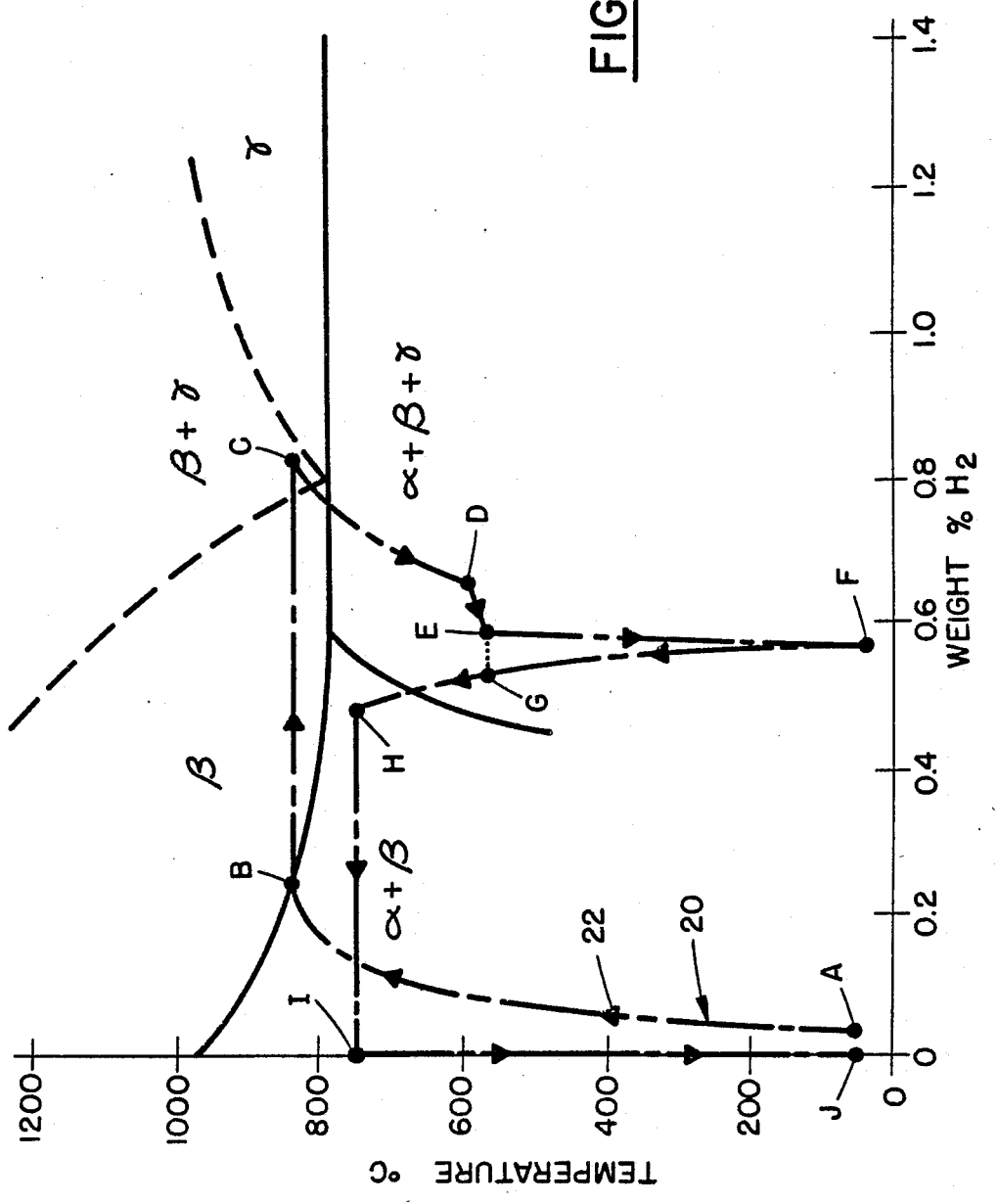
FIG. 1 is a (Ti-6Al-4V)-H phase diagram presenting the hydrogen concentrations and temperature ranges of interest for purposes of the invention.

The ultimate goal of joint replacement technology is to provide a resulting hybrid structure in which stress to the remaining bone will be as physiologic as possible: the joint must maintain its integrity and functionality within the constraints of a degrading environment while being subjected to cyclic loading. In order for this goal to be achieved (in the instance of the femoral component to a total hip arthroplasty, for example), it is necessary that stresses be successfully transferred from the stem to the surrounding bone tissue and through any intermediate materials. In turn, the replacement components must be properly affixed to the natural tissue. The historical development of fixation has been one of attempting to provide improved interfacial bonding and stress transfer between the different components within the constraints of material selection and design. It is the combination of stress levels and distribution, tissue remodeling and reaction to the implant materials, all functions of material selection and design, and of each other, which ultimately determine interfacial integrity and fixation.

In general, wrought metals have long been preferred over cast metals for surgical implants, particularly in high stress, intermittently loaded, regions as, for example, the hip. Indeed, wrought metals are recommended by ASTM for such a purpose.

At the same time, in recent years, there has been an ever greater emphasis on the development of implants which provide and promote tissue ingrowth in order to obtain a lasting and strong bonding between the artificial component and the natural bone sufficient to withstand the stresses to which the joint is subjected. For this purpose, porous coatings have been developed which provide a relatively thin but highly porous layer on the outer surface of the artificial component with the capability of promoting substantially complete integration of the component with the bone structure in which it is implanted. Such a concept is disclosed by Hahn in U.S. Pat. No. 3,605,123 which is said to have application to numerous metals which are typically used for medical prostheses. DePuy Division of Boehringer Mannheim Corporation utilizes a proprietary porous coating for joint implants which is identified by the trademark "POROCOAT".

Titanium alloys have long been preferred for joint implants which are highly stressed by reason of their material compatibility and their relative strength and light weight, particularly when the alloy combination includes aluminum and vanadium. A preeminent alloy used for such purposes is Ti-6Al-4V. Orthopedic articles so composed are preferably wrought in order to obtain optimum strength and fatigue characteristics. However, as previously noted, a substantial setback occurs when it is desired to apply by sintering a porous coating to such an article. Specifically, the thermal process generally necessary to bond a porous coating to a substrate metal requires the application of heat in the range of 200° C. to 1400° C. As a result, a lamellar microstructure is created which has inferior fatigue strength as compared with the wrought equiaxed microstructure recommended for surgical implants.

The process of the present invention, which is broadly referred to as a hydrogen alloying treatment (HAT), was conceived and has now been reduced to practice in an effort to overcome the previously explained impairment to sintered articles composed of titanium and, in particular, to titanium alloys. While it finds particular utility in treating titanium alloys with hydrogen, the invention should be operable by diffusion of materials other than hydrogen. The process is of particular benefit to surgical implants or other articles whose end uses require that they be subjected to high cyclic stressing. It is generally depicted by means of a preferred reaction pathway 20 and associated arrowheads 22 in FIG. 1 which is a phase diagram presenting temperature versus weight percent of hydrogen into Ti-6Al-4V. Relatively abrupt changes in direction of the pathway 20 are indicated, sequentially, by letters of the alphabet.

In the course of development of the inventive process, different cycles of the hydrogen alloying treatment sequence (hydrogenation, path A-B; beta transformation, path B-C; eutectoid decomposition, path C-D-E-F; and dehydrogenation, path F-G-H-I) were studied individually. The material used for the heat treatments and mechanical testing was 15.6 mm diameter forged annealed ELI (extra low interstitial) surgical grade Ti-6Al-4V bar stock. The chemical composition of the bar material, listed in Table 1, conformed to ASTM F136-84.

TABLE 1

| Chemical Composition of Ti-6Al-4V Bar Material | |
|---|---|
| Element | Weight % |
| $N_2$ | 0.018 |
| C | 0.014 |
| $H_2$ | 0.009 |
| Fe | 0.160 |
| $O_2$ | 0.120 |
| B | 0.001 |
| Cu | 0.002 |
| Si | 0.013 |
| Al | 6.1 |
| V | 4.2 |
| Ti | Balance |

Chemical analysis supplied by Titanium Metals Corporation of America

The mechanical properties, as reported by the manufacturer, are listed in Table 2, along with the minimum ASTM specification.

TABLE 2

| Mechanical Properties of Ti-6Al-4V Bar Material | | |
|---|---|---|
| | As-Received | ASTM-F136-84 |
| Yield Strength (MPa) | 893 | 795 |
| Ultimate Strength (MPa) | 993 | 860 |
| % Elongation | 18 | 10 |

TABLE 2-continued

Mechanical Properties of Ti-6Al-4V Bar Material

| | As-Received | ASTM F136-84 |
|---|---|---|
| % Reduction in Area | 42 | 25 |

Mechanical data supplied by Titanium Metals Corporation of America
Specimens 62.5 mm in length were cut from this stock. A length to diameter ratio of 4:1 was chosen to ensure that radial diffusion would be dominant.

Figure 2:
FIG. 2 is a photomicrograph (magnification: 200×) illustrating a post-sintered lamellar titanium alloy microstructure having alpha platelets in a beta matrix with grain boundary alpha being present.

Specimens were first sintered in the beta range (1100° C. 0.5 hr) at vacuum pressures of $10^{-5}$ to $-10^{-6}$ torr to minimize chemical contamination from the atmosphere and resulted in a lamellar microstructure. As seen in FIG. 2, the post-sintered lamellar microstructure consisted of alpha platelets in a beta matrix, with grain boundary alpha being present.

HYDROGENATION

The first step of the hydrogen alloying treatment sequence is the diffusion of hydrogen into the bulk metal. Two to four specimens per treatment were hydrogenated at 575°, 650°, 725° and 800° C. for 0.5, 1 and 2 hours, and at 850° C. (partial path A-B, FIG. 1) for 0.5 and 2 hours. See Table 3 below.

TABLE 3

Hydrogen Concentrations in Ti-6Al-4V Cylinders Following Hydrogenation

| Hydrogenation Treatment | Wt % $H_2$ |
|---|---|
| 575° C.-0.5 hr | 1.01 (0.06) |
| 575° C.-1.0 hr | 1.54 (0.07) |
| 575° C.-2.0 hr | 1.61 (0.09) |
| 650° C.-0.5 hr | 1.03 (0.00) |
| 650° C.-1.0 hr | 1.38 (0.15) |
| 650° C.-2.0 hr | 1.36 (0.01) |
| 725° C.-0.5 hr | 1.02 (0.09) |
| 725° C.-1.0 hr | 1.16 (0.02) |
| 725° C.-2.0 hr | 1.09 (0.03) |
| 800° C.-0.5 hr | 0.82 (0.03) |
| 800° C.-1.0 hr | 0.85 (0.01) |
| 800° C.-2.0 hr | 0.81 (0.07) |
| 850° C.-0.5 hr | 0.74 (0.05) |
| 850° C.-2.0 hr | 0.71 (0.04) |

Standard Deviations in ( )

Kerr et al, noted previously, report that eutectoid decomposition is optimized if hydrogen concentrations are 0.6-1.0 weight percent (wt. %) and achieving such easily controllable and reproducible concentrations was an object of our inventive process. At the temperatures of 800° C. and 850° C., we obtain such an easily controllable amount.

The environment of the specimens was then purged with argon at a flow rate of 10 SCFH (standard cubic feet per hour) for 30 minutes. Following purging, hydrogen was introduced at 10 SCFH. The compositions of the gases are listed in Table 4.

TABLE 4

Composition of Gases Used in Hydrogen Alloying Treatments (ppm)

| | $H_2$ | $N_2$ | $O_2$ | Hydrocarbons | $CO/CO_2$ | $H_2O$ |
|---|---|---|---|---|---|---|
| Ar | 2 | 10 | 2 | 2 | 2 | 10 |
| $H_2$ | — | 20 | 5 | 5 | 2 | 8 |

The partial pressure of all gases used in this study was one atmosphere. Hydrogen diffusion was controlled by maintaining constant the hydrogen partial pressure (1 atm) and flow rate (10 SCFH), and varying hydrogenation time and temperature. The equilibrium partial pressure of hydrogen in Ti-6Al-4V at the temperature and concentration of interest is 0.5 atm. Pressures greater than this allow for hydrogen diffusion to occur. Once a steady hydrogen flow was established, the specimens were heated to the hydrogenation temperature at a rate of 20°-25° C./min. After the hydrogenation temperature was reached, the hydrogen flow rate was increased to 20 SCFH. Temperatures were held constant to within 10° C. of the hydrogenation temperature. This part of the process is indicated by partial path B-C in FIG. 1.

As hydrogenation temperature increases, hydrogen diffusion decreases, and reaches an equilibrium concentration more rapidly. At 800° C. and 850° C., however, hydrogen concentrations are independent of hydrogenation time, indicating saturation at that temperature has occurred. This leads to three significant observations: first, a uniform hydrogen distribution can be assumed; second, an optimum concentration of hydrogen is achieved that renders the subsequent steps highly efficient and produces the optimum set of mechanical properties; and third, the problem of thermal stress cracking is resolved.

Indeed, several of the specimens treated at 575° C. and 650° C. were cracked, due to thermal stresses. Both longitudinal and circumferential cracks were observed. In their U.S. Pat. No. 4,680,063, Vogt et al suggest that slower cooling could avoid this problem. However, several specimens that were cooled at a slower rate (3.5% C./min vs. 30° C./min) were also cracked. Cracking is more a function of hydrogen content than cooling rate. Hydrogen embrittlement is attributed to the kinetics of hydrogen transport and its interaction with the saturated crystal lattice. Therefore, to avoid cracking, hydrogen concentrations should be below 1.5 wt. % and our procedure of treating at 800°-850° C. achieves this goal effectively.

Figure 3:
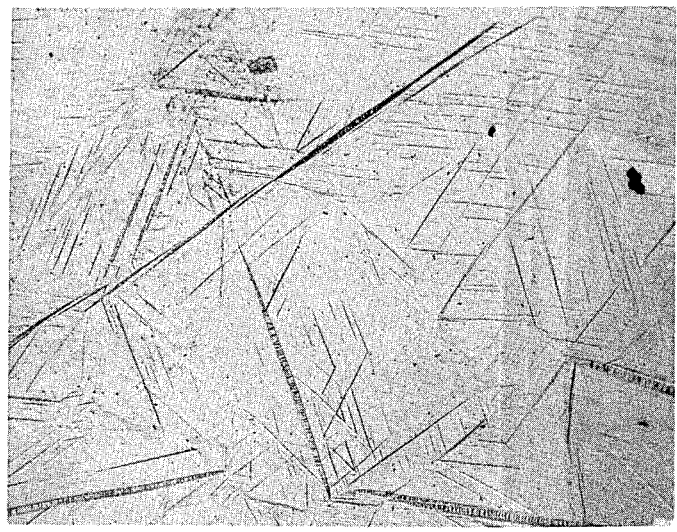
FIG. 3 is a photomicrograph (magnification: 100×) illustrating a mostly single phase beta microstructure containing titanium hydride (gamma) needles.
Figure 4:
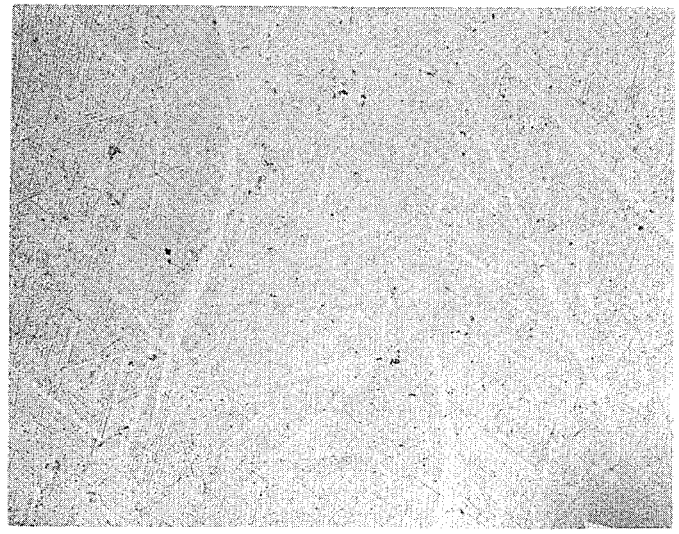
FIG. 4 is a photomicrograph (magnification: 100×) illustrating a titanium alloy microstructure which has been treated at 850° C. to yield a fully transformed beta microstructure.

Hydrogenation at 800° C. resulted in a mostly single-phase beta microstructure, containing titanium hydride (gamma) needles (FIG. 3). Isolated thin platelets of alpha plus beta were also present. In contrast, treatments at 850° C. yielded a fully transformed beta microstructure (FIG. 4). The thicker white platelets in the latter microstructure indicate a breakup of the alpha plus beta platelets which exist following hydrogenation at 800° C. The hydride needles are smaller at 850° C. as well. The hydrogen concentration following hydrogenation at 850° C. (0.74 wt. %) is lower than the concentration following hydrogenation at 800° C. (0.82 wt. %). The lower concentration is closer to the threshold concentration for hydride formation. Therefore, there is less hydride needle growth at higher temperatures. There are also fewer needles existing at the edge of the specimen, indicating a hydrogen gradient. Surface outdiffusion reduces the hydrogen concentrations to below the threshold level for hydride formation, and therefore the gamma phase is not present.

Specimens hydrogenated at 725° C. were found to have an untransformed alpha plus beta microstructure (not shown), indicating that this temperature is below the beta transformation temperature. Therefore, 800° C. is close to, or above, the beta transition temperature for hydrogen concentrations of 0.70-0.85 wt. %. This is similar to the findings of Kerr et al. referred to above. Hydrogenation and beta transformation are therefore combined into one thermochemical cycle, yielding a more efficient treatment. Kerr et al have used hydrogenation temperatures of 590° C.-650° C. This necessitates an extra treatment to create a beta transformation.

On the basis of amount of hydrogen diffused and the transformed microstructures, 850° C.-0.5 hour is found to be the optimum hydrogenation treatment. See Table 3. This treatment consistently yields hydrogen concentrations of approximately 0.75 wt. %, which is in the range considered optimal, as previously noted. Additionally, hydrogen reduces the beta transformation temperature, enabling a phase transformation to a fully beta microstructure at a lower than normal temperature with resulting energy conservation. The efficiency of the phase transformations in the subsequent treatment cycles are dependent on controlled hydrogenation, which in the present invention yield uniform microstructures in an optimized manner.

It was earlier mentioned, and is clearly seen in FIG. 1, that the beta transformation temperature and equilibrium eutectoid temperature of the (Ti-6Al-4V)-H system is 800° C. However, the most time efficient eutectoid temperature is 590° C. as previously noted. The slow kinetics of eutectoid decomposition permit existence of the (beta plus gamma) field below the eutectoid isotherm. Following hydrogenation and beta transformation, eutectoid treatments at 590° C. were employed. Again, see Table 5.

Specifically, following hydrogenation at 850° C. for 0.5 hour, specimens were cooled (3.5° C./min) to a eutectoid temperature of 590° C. in either an argon or hydrogen environment, at a flow rate of 10 SCFH. Eutectoid treatments, in argon or hydrogen environments, lasted 2 or 4 hours. Temperatures were kept constant to within 10° C. Upon completion of the eutectoid decomposition treatment, specimens were cooled in an argon atmosphere in the same manner as described previously.

EUTECTOID TRANSFORMATION

Following hydrogenation, specimens were cooled to room temperature at a moderate rate (30° C./min), in an argon environment (see Table 5 below and partial path C-D-E-F in FIG. 1).

TABLE 5

Eutectoid Decomposition Treatments Following Hydrogenation at 850° C.

| | Hydrog. Temp. | Cooling Rate from Hyd. Temp. | Eutect. Decomp. Treatment (E.D.T) | Cooling Rate from E.D.T. | Wt % H$_2$ |
|---|---|---|---|---|---|
| (1) | 850° C. | 3.5° C./min | 590° C.-2 hr/Ar | 30° C./min | 0.50(0.01) |
| (2) | 850° C. | 3.5° C./min | 590° C.-4 hr/Ar | 30° C./min | 0.50(0.03) |
| (3) | 850° C. | 3.5° C./min | 590° C.-8 hr/Ar | 30° C./min | 0.35 |
| (4) | 850° C. | 3.5° C./min | 590° C.-2 hr/H | 30° C./min | 1.68(0.06) |
| (5) | 850° C. | 3.5° C./min | 590° C.-4 hr/H | 30° C./min | 1.84(0.01) |
| (6) | 850° C. | 3.5° C./min | 590° C.-2 hr | 1° C./min | 0.52 |
| (7) | 850° C. | 3.5° C./min | 590° C.-2 hr | 50° C./min | 0.51 |
| (8) | 850° C. | 30° C./min | 590° C.-2 hr | 1° C./min | 0.72 |
| (9) | 850° C. | 30° C./min | 590° C.-2 hr | 50° C./min | 0.67 |
| (10) | 850° C. | 3.5° C./min | — | 30° C./min | 0.50 |

Standard Deviations ( )

The cooling cycle passes through a temperature range in which outdiffusion occurs (>500° C.). Slower cooling (3.5° C./min) following hydrogenation at 850° C. resulted in a 40% lower hydrogen content than more rapid cooling, indicating hydrogen outdiffusion. Hydrogen concentrations are independent of cooling rate for lower hydrogenation temperatures, since the range of temperature that specimens experience that induces outdiffusion is limited. If slower cooling is used, longer times are necessary to reduce the temperature below the threshold temperature for outdiffusion. Therefore at higher hydrogenation temperatures, cooling rate is more important. Too slow a cooling rate may result in the formation of an acicular alpha microstructure. In light of the need to maintain a controlled hydrogen distribution, moderate cooling rates (30° C./min) are advised. The problem may be avoided altogether, by employing consecutive cycles of hydrogenation and eutectoid decomposition (partial path C-D-E-G in FIG. 1), rather than cooling to room temperature following hydrogenation.

Subsequently, a series of treatments was performed to determine the effect of varying the cooling rate. Samples were hydrogenated at 850° C. for 0.5 hour, and then cooled at one of two rates (3.5° C./min, 30° C./min). Upon cooling to room temperature (partial path C-D-E-F, FIG. 1), the specimens were transferred to an air furnace already heated to the eutectoid temperature, and treated for 2 hours. It is noteworthy that the transfer of furnaces was arbitrary and is not critical to the invention. Upon completion of this last treatment, specimens were cooled at one of two rates (1° C./min, 50° C./min).

To uncouple the effects of cooling from the hydrogenation temperature to the eutectoid temperature from the effects of the eutectoid treatment itself, a group of specimens was hydrogenated (850° C.-0.5 hr), and cooled to 590° C. (3.5° C./min) (partial path C-D-E, FIG. 1). The specimens were then immediately cooled to room temperature (30° C./min, partial path E-F, FIG. 1), without ever undergoing a eutectoid treatment.

Figure 5:
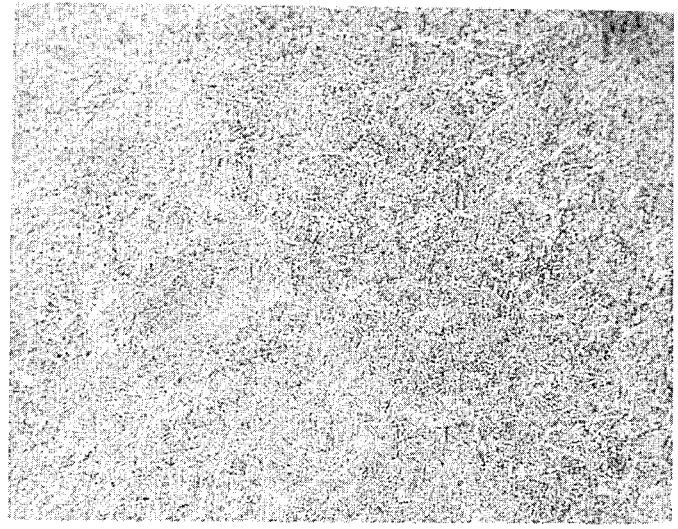
FIG. 5 is a photomicrograph (magnification: 500×) illustrating a titanium alloy microstructure which has been subjected to a eutectoid treatment at 590° C. illustrating massive nucleation of eutectoid alpha at the prior beta grain boundaries.

Eutectoid decomposition in an argon environment results in hydrogen outdiffusion. The observation that limited hydrogen outdiffusion occurred after eutectoid treatments of 2 hours, along with Kerr's data showing that transformation occurred after 2 hours at 0.56 wt. % hydrogen, implies that hydrogen outdiffusion (0.25 wt. %) occurs early in the eutectoid treatment, or during cooling from the hydrogenation temperature. Therefore treatments at 590° C. reflect eutectoid decomposition cycles at constant hydrogen levels (0.4–0.7 wt. %). Eutectoid treatments at these hydrogen concentrations promote massive nucleation of eutectoid alpha at the prior beta grain boundaries (FIG. 5). The resulting microstructures are very fine 2-phase (alpha plus beta) structures, with some gamma remaining, depending on local hydrogen concentrations. Transformation is more complete at the specimen periphery, implying hydrogen concentrations are different here. In these regions, a primarily alpha microstructure exists, with very few prior beta grains remaining, indicating complete transformation. The alpha grains are more elongated here. Since grain growth is unlikely at this temperature, the surface hydrogen concentration must be lower. As a result of this, a less than optimal eutectoid reaction occurs. Treatments lasting eight hours resulted in further hydrogen outdiffusion and more grain growth, also in the form of alpha needle elongation. Decomposition is less efficient with lower hydrogen concentrations (0.31 wt. %), leading to a coarser grain morphology, with elongated and thickened alpha grains.

The optimum treatments were the hydrogenation-beta-transformation/eutectoid decomposition treatments of 850° C.-0.5 hr/590° C.-4 hr in an argon environment (partial path A-B-C-D-E-(F)-G, FIG. 1). These treatments yield an extremely fine and uniform (alpha plus beta) microstructure. The remaining hydrogen concentration (0.50 wt. %) is high enough to effectively transform the microstructure, yet low enough to produce efficient outdiffusion during dehydrogenation.

DEHYDROGENATION

Eutectoid transformation refines the grain structure. Nonetheless, the remaining hydrogen (0.5-0.8 wt. %) must be outdiffused to avoid mechanical property degradation. Since hydrogen concentrations are below threshold values for hydride formation, hydrogen is undetectable in the microstructure (FIG. 5). Residual hydrogen concentrations are known to compromise mechanical integrity, as applied stress causes hydrogen to diffuse to areas of triaxiality. However, there is no effect of hydrogen on dynamic properties as long as concentrations are below approximately 110 ppm. Accordingly, the maximum allowable concentration for wrought Ti-6Al-4V is 120 ppm (0.012 wt. %) as established by ASTM F136-84. Unfortunately, a caveat to the necessity of dehydrogenation is that the treatments necessary to cause dehydrogenation cause grain growth, which reduces strength.

Dehydrogenation treatments were first performed on 5 mm thick disks cut from cylindrical specimens which had been given a consecutive hydrogenation/eutectoid decomposition treatment. The hydrogen concentrations prior to dehydrogenation used at that time were 0.51 wt. % (see Table 3). The eutectoid decomposition treatment results in a mostly uniform microstructure. It is therefore assumed that hydrogen concentrations in all sections of a specimen are equivalent.

For this phase of the study, cylindrical samples which underwent eutectoid decomposition treatments (1) and (2) of Table 5 were sectioned into the 5 mm thick disks mentioned above. As presented in Table 6 below, two disks each were dehydrogenated in vacuum at 600°, 650°, 750° and 800° C. for 2 hours, and 700° C. for 0.5, 1 and 2 hours. Two specimens each also underwent two-phase hydrogenation/dehydrogenation cycles of 850° C.-0.5 hr/600° C.-C.-8 hr and 850° C.-0.5/700° C.-2 hr.

TABLE 6

Hydrogen Concentrations in Disks Following Dehydrogenation

| Treatment | Wt % $H_2$ | Wt % $H_2$ Following 925° C.-4 hr |
|---|---|---|
| 600° C.-2.0 hr | 0.163 (0.001) | 0.002 (0.003) |
| 600° C.-8.0 hr | 0.030 | n.d.* |
| 650° C.-2.0 hr | 0.079 (0.005) | 0.002 (0.003) |
| 700° C.-0.5 hr | 0.058 (0.007) | 0.008 (0.000) |
| 700° C.-1.0 hr | 0.038 (0.004) | 0.001 (0.001) |
| 700° C.-2.0 hr | 0.018 (0.011) | 0.007 (0.007) |
| 750° C.-2.0 hr | 0.017 (0.009) | 0.013 (0.007) |
| 800° C.-2.0 hr | 0.006 (0.005) | 0.005 (0.006) |

Standard deviations in ( ); *n.d. = not determined

Dehydrogenation was performed in a vacuum furnace which was initially evacuated to $10^{-6}$ to $10^{-7}$ torr, and maximum pressures of $10^{-4}$ to $10^{-5}$ torr were subsequently maintained. To minimize the effects of dehydrogenation during heating in vacuum, the heating rate was increased from 3.5° C./min to 10° C./min at 500° C., the temperature at which dehydrogenation starts. After dehydrogenation, specimens were furnace cooled to room temperature (5° C./min), as indicated by partial path I-J, FIG. 1.

After the parametric effects of temperature and time on dehydrogenation were determined for the disk specimens, dehydrogenation treatments were performed on the larger cylindrical specimens. These treatments, presented in Table 7, were: (1) 600° C.-8,16,24 hrs and 650° C.-8,16 hrs (following hydrogenation at 850° C.-0.5 hr) and (2) 775° C.-2,4 hrs, as indicated by partial path H-I, FIG. 1 (following treatment (2) presented in Table 5).

TABLE 7

Hydrogen Concentrations in Cylinders Following Dehydrogenation

| Dehydrogenation Treatment | Average Wt % $H_2$ |
|---|---|
| 600° C.-8 hr | 0.0754 (0.0072) |
| 600° C.-16 hr | 0.0327 (0.0064) |
| 600° C.-24 hr | 0.0357 (0.0058) |
| 650° C.-8 hr | 0.0236 (0.0000) |
| 650° C.-16 hr | 0.0496 (0.0558) |
| 775° C.-4 hr | 0.0203 (0.0069) |
| 800° C.-2 hr | 0.0167 (0.0010) |

Standard Deviations in ( )

Following dehydrogenation, a group of specimens was given a vacuum annealing treatment (925° C.-4 hrs), known to cause total dehydrogenation. The total concentration of hydrogen outdiffused is equal to the sum of the hydrogen concentrations outdiffused from the two vacuum treatments (Table 6). The calculated weight losses are consistently 0.49-0.50 wt. %, verifying that the hydrogen concentrations remaining following dehydrogenation were correctly determined. This also verifies the assumption that hydrogen concentrations are constant throughout the specimen.

Dehydrogenation occurs more readily at higher temperatures. Treatments of two hours at temperatures 700° C., or greater, are sufficient to dehydrogenate disks to an acceptable hydrogen level. The data for the different treatment times at 700° C. implies that most of the hydrogen is outdiffused in the first 0.5 hour. Dehydrogenation is incomplete at lower temperatures and shorter times. This is due to the slower diffusion kinetics, which are proportional to the square root of the third power of temperature. Therefore, greater dehydrogenation times are needed at lower temperatures. Dehydrogenation temperatures and times must be chosen with the constraint of minimizing grain growth. Grain growth is minimized if shorter times are used, the opposite requirement of efficient dehydrogenation.

Following dehydrogenation, a very fine and uniform microstructure can be attained (not shown) which resembles a broken-down basketweave structure. The prior beta grain boundaries are retained from the beta-transformation and form colony boundaries of alpha phase. The orientation of the structure within colonies is uniform. Lower dehydrogenation temperatures produced finer microstructures, with a discontinuous beta phase and little or no prior beta grain boundary alpha. The grain boundary alpha that did nucleate was not continuous. Higher dehydrogenation temperatures produced alpha grain growth. Alpha grain growth takes the form of needle elongation first, and then a fattening of the grains.

Two-step beta transformation-hydrogenation/eutectoid transformation-dehydrogenation treatments (850° C.-0.5 hr/600°-650° C.) were also found to refine the microstructure significantly. These microstructures are slightly coarser and have slightly larger alpha platelets. The nucleated alpha in this instance appears to be less rounded than the eutectoid alpha produced during treatment at 590° C., possibly implying a different transformation reaction. The more rounded morphology could be due to the added aging time at 590° C. The intermediate aging step also serves to outdiffuse approximately 0.25 wt. % hydrogen, making dehydrogenation more efficient. This is accomplished without grain growth.

Dehydrogenation of the small disks provided parametric data on the efficiency of treatments, and lower bounds on the refined alpha grain size. Dehydrogenation treatments were next performed on larger cylindrical specimens. This verified the assumption that hydrogen concentrations are the same in any section of a specimen. It also determined the effects of specimen size on dehydrogenation. Table 7 presents these results, for average hydrogen concentrations of 0.65-0.75 wt. % prior to dehydrogenation.

There is an effect of specimen size on dehydrogenation. The optimal parameters for the most efficient treatment, and final grain size depend on dimensions of the component. The dehydrogenation treatments will not be as efficient for larger, more complex components, such as joint replacements. Specimens dehydrogenated at 600° C. for 8 hours retain an order of magnitude more hydrogen than disks subjected to a similar treatment. Tripling the treatment time at 600° C. still does not produce sufficient hydrogen outdiffusion for mechanical feasibility. Dehydrogenation treatments of 650° C. may be used, without much microstructural compromise, since aging at these temperatures doesn't promote much grain growth.

Aside from the parameters controlling the kinetics of dehydrogenation namely, temperature and time, there is the manufacturing parameter of pump efficiency. Specifically, the pump apparatus associated with the furnace must be able to efficiently remove the evolved hydrogen, without altering the treatment cycle or risking furnace contamination from elevated pressures.

Figure 6:
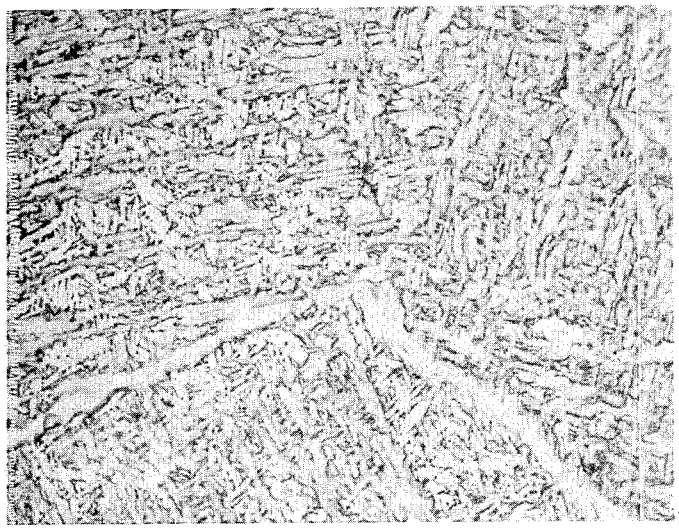
FIG. 6 is a photomicrograph (magnification: 1000×) illustrating a titanium alloy microstructure present after being subjected to a dehydrogenation treatment at 775° C. for a duration of 4 hours.

Dehydrogenation treatments were considered acceptable if residual hydrogen concentrations were below 120-150 ppm, and if grain growth didn't compromise the refinement previously established. The two treatments chosen for mechanical testing were: (1) 650° C.-16 hr and (2) 775° C.-4 hr (FIG. 6). The treatments resulted in respective grain sizes following dehydrogenation of 0.9 microns for treatment (1) and 1.3 microns for treatment (2), a significant improvement over the lamellar grain size of 4.0 microns. The original grain size of the equiaxed microstructure was 3.4 microns. In addition to reducing resulting grain size, the aspect ratio of the alpha grains is also desirably reduced.

Treatment (1) is matter of factly a combined eutectoid decomposition and dehydrogenation treatment. It yields an extremely fine and uniform microstructure, with rounded alpha grains. The low dehydrogenation temperature prevented the formation of grain boundary alpha. A temperature of 775° C. was used for the second treatment. A dehydrogenation too close to the beta transus (800 ° C.) might cause a transformation back to a beta structure. The microstructures resulting from the second treatment show grain growth in the form of platelet elongation and thickening, and discontinuous grain boundary alpha. There is more beta present than in the microstructures developed at lower dehydrogenation temperatures, and there is less order to the broken down basketweave. The microstructure is uniform with respect to location.

THE APPLICATION OF HAT TO TOTAL JOINT REPLACEMENTS

The application of the hydrogen alloying treatments to total joint replacements introduces three important variables which merit consideration: (1) sintering temperature, (2) the porous coating, and (3) component size. Table 8 summarizes the results of a parametric study of these variables.

TABLE 8

Effect of Sintering Temperature, Specimen Size and Porous Coating on Hydrogen Alloying Treatments

| | Specimen Length | Hydrogen Alloying Treatment | Wt % $H_2$ |
|---|---|---|---|
| Effect of Sintering Temperature and Specimen Size | | | |
| Sintering Treatment | | | |
| 1100° C.-0.5 hr | 62.5 mm | 850° C.-0.5 hr | 0.74(0.05) |
| 1370° C.-4.0 hr | 62.5 mm | 850° C.-0.5 hr | 0.73(0.11) |
| 1100° C.-0.5 hr | 5 mm | 850° C.0-5 hr | 0.66(0.01) |
| 1370° C.-4.0 hr | 5 mm | 850° C.-0.5 hr | 0.64(0.01) |
| 1100° C.-0.5 hr | 62.5 mm | 850° C.-0.5 hr/590° C.-4 hr | 0.50(0.01) |
| 1370° C.-4.0 hr | 62.5 mm | 850° C.-0.5 hr/590° C.-4 hr | 0.65(0.00) |
| 1100° C.-0.5 hr | 5 mm | 850° C.-0.5 hr/590° C.-2 hr | 0.33(0.05) |
| 1100° C.-0.5 hr | 5 mm | 850° C.-0.5 hr/590° C.-4 hr | 0.33(0.04) |
| 1370° C.-4.0 hr | 5 mm | 850° C.-0.5 hr/590° C.-2 hr | 0.32(0.03) |
| 1370° C.-4.0 hr | 5 mm | 850° C.-0.5 hr/590° C.-4 hr | 0.28(0.04) |
| Effect of Porous Coating and Specimen Size | | | |
| Specimen Type | | | |
| uncoated | 3.25 mm | 850° C.-0.5 hr | 0.75 (0.00) |
| porous coated | 3.25 mm | 850° C.-0.5 hr | 0.75 (0.07) |
| uncoated | 100 mm | 850° C.-0.5 hr | 0.75 (0.05) |
| porous coated | 100 mm | 850° C.-0.5 hr | 0.79 (0.03) |
| uncoated | 3.25 mm | 850° C.-0.5 hr/590° C.-4 hr | 0.28 (0.04) |
| porous coated | 3.25 mm | 850° C.-0.5 hr/590° C.-4 hr | 0.39 (0.11) |
| uncoated | 100 mm | 850° C.-0.5 hr/590° C.-4 hr | 0.64 (0.03) |
| porous coated | 100 mm | 850° C.-0.5 hr/590° C.-4 hr | 0.65 (0.02) |

Standard Deviations in ( )

As clearly seen from a study of Table 8, hydrogen diffusion is independent of sintering temperature. Upon microscopic examination, the expected result was that lamellar alpha platelets are thinner if sintering temperatures are lower and sintering times are shorter, and there are more grain boundaries for a similar volume fraction of beta. The fact that hydrogen diffusion does not change appreciably with sintering temperature indicates that hydrogen preferentially diffuses into the BCC beta matrix rather than the grain boundaries. Hydrogenation following sintering at 1370° C. is found to yield the same microstructure following hydrogenation at lower sintering temperatures, i.e. 1100° C. The (beta plus gamma) platelets are longer and thicker, and have more of a two-dimensional morphology. Several platelets have second phases, and there are also hydride needles within the larger platelet-like structure. The length, thickness and concentrations of these needle-like phases varies, but there is no location dependence, implying no hydrogen gradient.

Similarly, eutectoid decomposition is independent of sintering temperature. This is to be expected, since this treatment phase is dependent upon hydrogenation. Thus, hydrogenating above the beta transition temperature homogenizes the microstructure.

Hydrogen concentrations do not change much with specimen size or with the addition of a porous coating, implying, as stressed before, that hydrogen saturation exists. For larger and more complex components, such as joint replacements, longer hydrogenation times may be necessary to reach saturation conditions.

Hydrogen content following eutectoid decomposition is also dependent upon component size. Hydrogen outdiffusion occurs more readily in smaller components. The result of this is that the nose of the temperature-time-eutectoid transformation (TTT) curve is bypassed, and coarser lamellar platelets are nucleated rather than fine eutectoid alpha. Therefore, a tight range of hydrogen concentrations is necessary to achieve an optimal eutectoid transformation. Larger components will therefore require longer aging times at the eutectoid temperature. As discussed above there is also a pronounced effect of component size on dehydrogenation. In light of the dependence of the treatment sequence on section size, grain refinement in joint replacements may be compromised if not properly controlled.

Figure 7:
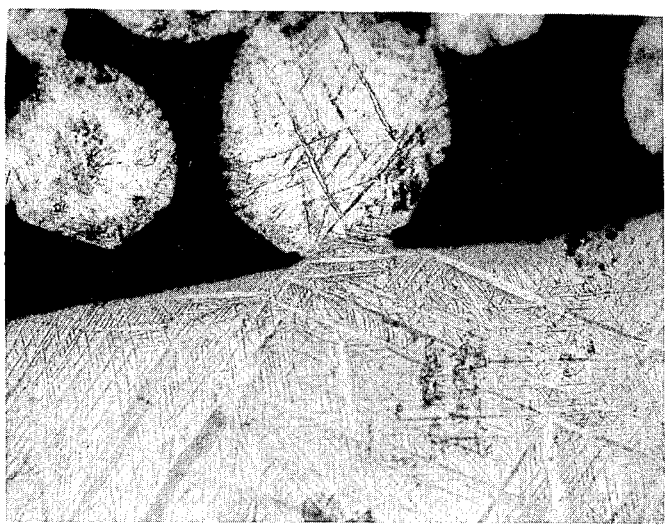
FIG. 7 is a photomicrograph (magnification: 200×) illustrating a titanium alloy microstructure illustrating the substrate region of a porous coated specimen following hydrogenation which is characterized by thin platelets and hydride.

Following hydrogenation, the substrate region of porous coated specimens exhibits the characteristic platelets morphology. The platelets are thinner than in the uncoated specimens, and there are no second phases present. There are, however, more hydride needles, varying in number, size and density. The microstructure in the porous coating is characterized by thin platelets and hydride (FIG. 7). There appears to be more hydride in the porous coating than in the substrate, implying preferential hydrogen diffusion into the coating. This to be be expected, since the diffusion coefficient of pure titanium is known to be greater than that of titanium alloy. The region of the coating closest to the substrate looks similar to the substrate, since there is a diffusion of alloying elements into the coating during sintering. Also, regions of the coating are starting to transform to the eutectoid structure.

No cracks were detected in the hydrogenated porous coated specimens which were studied. This condition indicates a significant benefit of the invention, as we previously indicated.

Figure 8:
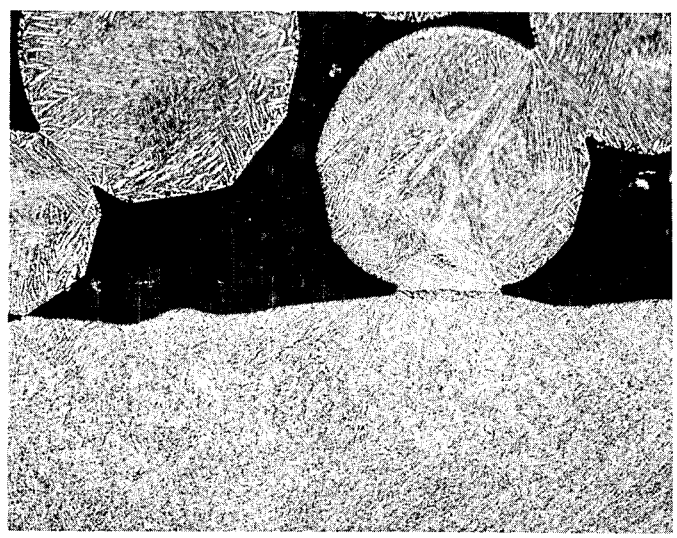
FIG. 8 is a photomicrograph (magnification: 200×) illustrating a titanium alloy microstructure, similar to FIG. 7 but illustrating the characteristic broken up Widmanstatten microstructure present following eutectoid decomposition.

Following eutectoid decomposition, porous coated specimens were found to exhibit the characteristic microstructure reminiscent of a broken up basket weave structure (FIG. 8). There are elongated alpha platelets at the edges of the beads, and at the coating/substrate interface. This less than optimal eutectoid transformation is presumably due to local variations in hydrogen concentration.

Figure 9:
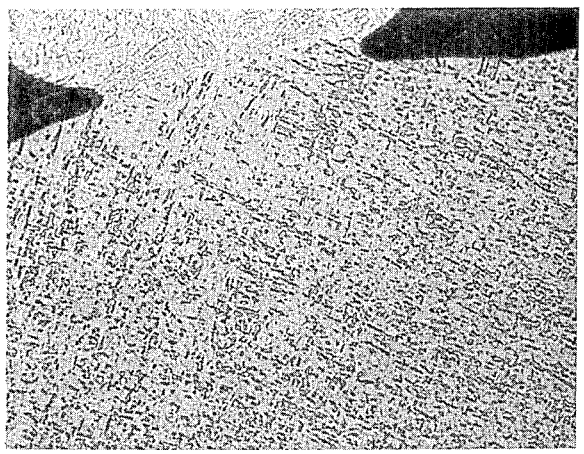
FIG. 9 is a photomicrograph (magnification: 400×) illustrating a titanium alloy microstructure similar to FIGS. 7 and 8, but depicting the resulting microstructure in the porous coated specimens which is the same uniquely fine microstructure obtained in the uncoated specimens.

Upon dehydrogenation, however, the resulting microstructure in the porous coated specimens is the same uniquely fine microstructure obtained in the uncoated specimens. This is a microstructure heretofore unattainable in beta-annealed Ti-6Al-4V (see FIG. 9).

In general, therefore, it has been found that there are only minimal differences between porous coated and uncoated materials as far as the hydrogen alloying treatments are concerned, and the porous coating does not alter the treatment cycles.

MECHANICAL PROPERTIES OF TI-ALLOY COMPONENTS SUBJECTED TO HAT

Figure 10:
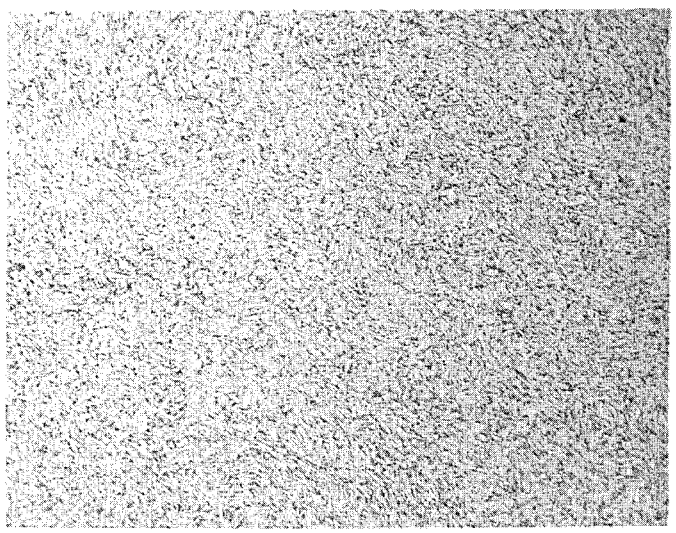
FIGS. 10 and 11 are photomicrographs (magnification: 200×) illustrating the microstructures of two of the titanium alloy specimens subjected to tensile testing, specifically, the equiaxed and the HAT-2 microstructures.
Figure 11:
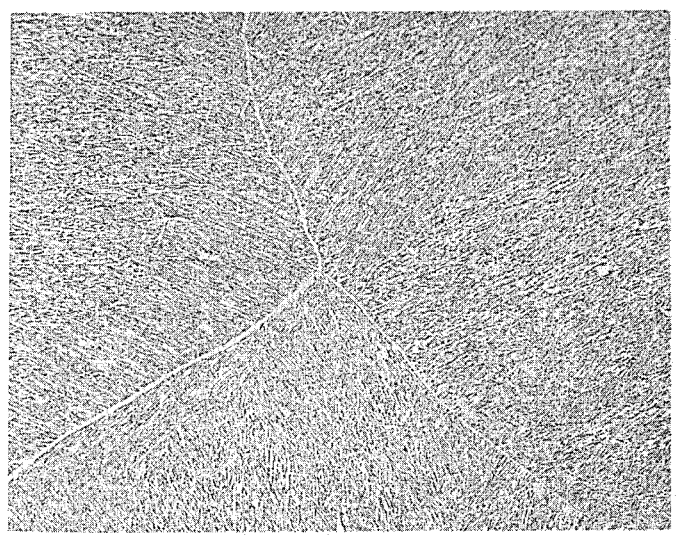

Tensile testing was performed on specimen groups from each of five microstructures, specifically, equiaxed (E), lamellar sintered 1370° C.-4 hrs (L), and three subjected to post-sintered hydrogen alloying treatment (HAT). All of the specimens were tested to failure and the results of the testing are presented in Table 9 below. The microstructures of the group subjected to the hydrogen alloying treatment are referred to, respectively, as HAT-1, HAT-2, and HAT-3, and the specific treatment accorded each is recited in the table. Photomicrographs of the HAT-1, equiaxed, and HAT-2 microstructures are presented, respectively, in FIGS. 9, 10, and 11.

TABLE 9

Tensile Properties For Different Ti-6Al-4V Microstructures

| Microstructure | YS (MPa) | UTS (MPa) | % RA |
| --- | --- | --- | --- |
| EA (n = 6) | 914 (8) | 1000 (14) | 39.6 (1.0) |
| L (n = 5) | 902 (53) | 994 (33) | 14.4 (3.5) |
| HAT-1 (n = 4) | 1119 (53) | 1152 (48) | 11.3 (5.5) |
| HAT-2 (n = 3) | 1011 (29) | 1072 (21) | 19.0 (3.2) |
| HAT-3 (n = 6) | 974 (32) | 1025 (48) | 12.3 (2.8) |

Legend:
EA = Equiaxed, L = Lamellar,
HAT-1 = Post-sintered hydrogen alloy treated as follows: beta transformation - hydrogenation/eutectoid transformation - dehydrogenation 850° C.-0.5 hr/650° C.-16 hrs (vacuum)
HAT-2 = Post-sintered hydrogen alloy treated as follows: beta transformation - hydrogenation/eutectoid transformation/dehydrogenation 850° C.-0.5 hr/590° C.-4 hr(Ar)/800° C.-2 hrs (vacuum)
HAT-3 = Post-sintered hydrogen alloy treated as follows: beta transformation - hydrogenation/eutectoid transformation/dehydrogenation 850° C.-0.5 hr/590° C.-4 hr(Ar)/775° C.-4 hrs (vacuum)
YS = Yield Strength, UTS = Ultimate Tensile Strength,
% EL = Percent Elongation, % RA = Percent Reduction in Area
Standard Deviations in ( )

A review of the data presented in Table 9 indicates that the HAT microstructures possess yield strengths and ultimate tensile strengths moderately greater than the EA microstructure and present still further improvements over the lamellar microstructure. It is noteworthy that percent reduction in area, as presented in Table 9, is a proper measure of ductility of a material. In this regard, it is further noted that the percent reduction in area of both the lamellar and the HAT microstructures is acceptable for medical prosthesis use. While it is acknowledged that the equivalent value for the EA microstructure is substantially greater than an acceptable value, nevertheless, in terms of yield strength and ultimate tensile strength the HAT microstructures are clearly superior.

The sequence of steps which results from this invention produces a highly efficient process in terms of both energy efficiency and labor efficiency. The optimum hydrogenation step is very short in duration and produces the best kinetics for the subsequent entectoid decomposition reaction. Furthermore, the process is very versatile as a result of which efficiency can be obtained by adjusting the steps of the industrial process in keeping with minimized costs of labor and capital. For instance, our process produces an article, after the hydrogenation step, which can either be maintained at temperature in the same furnace or can be cooled down to room temperature and transferred to another furnace.

Fatigue testing was also performed on four of the five specimen groups subjected to tensile testing. The results of the fatigue testing are presented in Table 10. Clearly, the uncoated specimen groups subjected to the treatment of the invention exceed not only the lamellar group in that category, but also the equiaxed group. These results are explained by the facts that (1) we refined the alpha grain size and (2) reduced the aspect ratio of the alpha grains.

TABLE 10

Summary of Rotating Bending Fatigue Data

| Sample Group | Fatigue Strength (MPa) |
| --- | --- |
| Uncoated: equiaxed | 590 (9) |
| lamellar | 497 (7) |
| HAT-1 | 669 (51) |

TABLE 10-continued

Summary of Rotating Bending Fatigue Data

| Sample Group | Fatigue Strength (MPa) |
|---|---|
| HAT-3 | 643 (7) |
| Porous Coated: lamellar | 218 (8) |
| HAT-3 | 177 (9) |

Standard Deviations in ( )

The fatigue data from the porous coated specimens shown in Table 10 show a slight difference only between the lamellar and HAT-3 microstructures. This is due to the overwhelming effect of the stress concentrators present in the porous coating geometry tested. However, a joint prosthesis is not customarily covered on 100% of its surface by a porous coating. Highly stressed areas are not porous coated and it is for those areas that the HAT-3 treatment produces a 30% higher fatigue strength than an article having a lamellar microstructure immediately after the sintering operation.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. A process of treating an article composed of titanium alloy comprising the steps of:
   (a) heating the article to a temperature generally in the range of 800° C. to 1000° C.;
   (b) diffusing hydrogen into the article until the concentration of hydrogen in the article is an amount in the range of approximately 0.5% to 1.0% by weight, the hydrogen inducing the phase transformation of the article to a fully beta$_H$ or beta$_H$ plus gamma microstructure where beta$_H$ is the beta microstructure substantially completely saturated with hydrogen;
   (c) cooling the article in an inert atmosphere to a temperature below the beta transus;
   (d) maintaining the article at a temperature below the beta transus and for a duration adequate to achieve a eutectoid decomposition transformation so as to produce a fine and uniform alpha plus beta or alpha plus beta plus gamma microstructure with a distinctly non-lamellar morphology;
   (e) reducing the concentration of hydrogen in the article to an amount below approximately 120 to 150 ppm; and
   (f) cooling the article to room temperature.

2. A process as set forth in claim 1 wherein step (a) is performed at a temperature in the range of approximately 800° C. to 900° C.

3. A process as set forth in claim 1 wherein step (a) is performed at a temperature in the range of approximately 840° C. to 860° C.

4. A process as set forth in claim 1 wherein in step (c) the article is cooled to room temperature.

5. A process as set forth in claim 1 wherein steps (a) and (b) are performed simultaneously.

6. A process as set forth in claim 1 wherein step (b) does not commence until the temperature rang of step (a) has been reached.

7. A process as set forth in claim 1 wherein step (b) does not commence until the temperature range of 800° C. to 900° C. has been reached.

8. A process as set forth in claim 1 wherein step (b) does not commence until the temperature range of 840° C. to 860° C. has been reached.

9. A process as set forth in claim 1 wherein step (c) is performed in an atmosphere of argon gas.

10. A process as set forth in claim 1 wherein the article is composed substantially of Ti-6Al-4V.

11. A process as set forth in claim 1 wherein the article is composed substantially of extra low interstitial (ELI) grade Ti-6Al-4V.

12. A process as set forth in claim 1 wherein steps (d) and (e) are performed simultaneously.

13. A process as set forth in claim 1 wherein hydrogen is diffused into the article in an amount in the range of 0.70% to 0.90% by weight.

14. A process as set forth in claim 1 wherein step (b) is performed at a temperature in the range of approximately 800° C. to 900° C. for a duration of approximately one-half hour.

15. A process as set forth in claim 1 wherein step (b) is performed at a temperature in the range of approximately 840° C. to 860° C. for a duration of approximately one-half hour.

16. A process as set forth in claim 1 wherein step (d) is performed in an inert atmosphere at a temperature in the range of approximately 575° C. to 600° C. for a duration of approximately one to six hours.

17. A process as set forth in claim 1 wherein step (d) is performed in an inert atmosphere at a temperature in the range of approximately 575° C. to 675° C. for a duration of approximately one to 24 hours; and 18. A process as set forth in claim 1 wherein step (e) is performed at a temperature of less than 800° C. for a duration of up to 24 hours.

19. A process as set forth in claim 1 wherein step (e) is performed at a temperature in the range of approximately 765° C. to 785° C. for a duration of approximately 4 hours.

20. A process as set forth in claim 1 wherein step (d) and (e) are performed simultaneously in an inert atmosphere at a temperature in the range of 640° C. to 680° C. for a duration of approximately four to 24 hours.

21. A process as set forth in claim 1 wherein the article has previously been sintered.

22. A process as set forth in claim 10 wherein the inert atmosphere utilized in step (d) is one of argon gas.

23. A titanium alloy article treated by the process of claim 1.

24. A sintered titanium alloy article treated by the process of claim 1.

25. An article composed substantially of Ti-6Al-4V treated by the process of claim 1.

26. A sintered article composed substantially of Ti-6Al-4V treated by the process of claim 1.

27. A medical prosthesis composed of titanium alloy treated by the process of claim 1.

28. A medical prosthesis composed of sintered titanium alloy treated by the process of claim 1.

29. A medical prosthesis composed substantially of Ti-6Al-4V treated by the process of claim 1.

30. A medical prosthesis composed substantially of sintered Ti-6Al-4V treated by the process of claim 1.

31. A medical prosthesis set forth in claim 30 having a substantially porous outer surface.

32. A sintered article composed of titanium alloy subjected to the treatment as set forth in claim 1 and having a nominal resulting grain size smaller than one micron across.

33. A sintered article composed substantially of Ti-6Al-4V subjected to the treatment as set forth in claim 1 and having a nominal resulting grain size smaller than one micron across.

34. A sintered medical prosthesis composed of titanium alloy subjected to the treatment as set forth in claim 1 and having a nominal resulting grain size smaller than one micron across.

35. A sintered medical prosthesis composed substantially of Ti-6Al-4V subjected to the treatment as set forth in claim 1 and having a nominal resulting grain size smaller than one micron.

36. A sintered medical prosthesis as set forth in claim 35 having a substantially porous outer surface.

37. A sintered article composed of hydrogen treated titanium alloy which, at ambient temperature exhibits a fine and uniform alpha plus beta or alpha plus beta plus gamma microstructure with a distinctly non-lamellar morphology and has a yield strength and an ultimate tensile strength at least equivalent to that of a similar non-sintered titanium alloy article having an equiaxed microstructure.

38. A sintered article as set forth in claim 36 being composed substantially of Ti-6Al-4V.

39. A sintered article as set forth in claim 37 having a substantially porous outer surface.

40. A process of treating a titanium alloy article comprising the steps of:
(a) heating the article to a temperature generally in the range of 800° C. to 1000° C.;
(b) diffusing a gaseous solute into the article during the heating step until the article has become substantially saturated with the solute, the solute inducing the phase transformation of the article to a fully $beta_S$ microstructure where $beta_S$ is the beta microstructure substantially completely saturated with the gaseous solute;
(c) cooling the article in an inert atmosphere to a temperature below the beta transus;
(d) maintaining the article at a temperature below the beta transus and for a duration adequate to achieve a eutectoid decomposition transformation so as to produce a fine and uniform alpha plus beta microstructure with a distinctly non-lamellar morphology;
(e) substantially removing the gaseous solute from the article; and
(f) cooling the article to room temperature.

41. An uncoated titanium alloy article produced by the process recited in claim 1 exhibiting a yield strength of at least 950 MPa, an ultimate tensile strength of at least 1000 MPa, and a fatigue strength of at least 630 MPa.

* * * * *